United States Patent
Bobo, Jr. et al.

[11] Patent Number: 5,230,342
[45] Date of Patent: Jul. 27, 1993

[54] BLOOD PRESSURE MONITORING TECHNIQUE WHICH UTILIZES A PATIENT'S SUPRAORBITAL ARTERY

[75] Inventors: Donald E. Bobo, Jr., Orange, Calif.; Dwayne R. Westenskow; Phillip D. Baker, both of Salt Lake City, Utah

[73] Assignee: Baxter International Inc., Deerfield, Ill.

[21] Appl. No.: 752,399

[22] Filed: Aug. 30, 1991

[51] Int. Cl.⁵ ............... A61B 5/0225; A61B 5/022
[52] U.S. Cl. .......................... 128/677; 128/686; 128/672
[58] Field of Search ............ 128/672, 686, 714, 677, 128/678, 679, 681, 691

[56] References Cited

U.S. PATENT DOCUMENTS

| | | | |
|---|---|---|---|
| 2,989,051 | 6/1961 | Zuldema et al. | 128/205 |
| 3,040,737 | 6/1962 | Kompelien et al. | |
| 3,658,054 | 4/1972 | Iberall | 128/672 |
| 3,704,708 | 12/1972 | Iberall | 128/205 |
| 3,903,872 | 2/1974 | Link | 128/205 |
| 4,007,734 | 2/1977 | Peters | 128/677 |
| 4,009,709 | 3/1977 | Link et al. | 128/205 |
| 4,074,711 | 2/1978 | Link et al. | 128/205 |
| 4,559,953 | 12/1985 | Wright et al. | 128/680 |
| 4,703,758 | 11/1987 | Omura | 128/672 |
| 5,022,402 | 6/1991 | Schieberl et al. | 128/671 |

FOREIGN PATENT DOCUMENTS

| | | | |
|---|---|---|---|
| 0247880 | 12/1987 | European Pat. Off. | 128/672 |
| 0326384 | 1/1989 | European Pat. Off. | |
| 0705933 | 3/1966 | Italy | 128/677 |
| 0238076 | 7/1969 | U.S.S.R. | 128/672 |

*Primary Examiner*—Randall L. Green
*Assistant Examiner*—D. Willse
*Attorney, Agent, or Firm*—Stephen C. Shear; Bruce M. Canter

[57] ABSTRACT

There is disclosed herein a method of obtaining certain information about the blood pressure of a given patient by means of a particular blood pressure technique, specifically by means of oscillometry, in which the pressurizable pressure transducing bladder located adjacent and cooperating with a particular artery of the patient, is used in combination with means for pressurizing the bladder in a controlled way in order to provide the desired information. The particular artery used is the patient's supraorbital artery which is readily accessible in a specific area just above the eyebrow of substantially all patients. There is also disclosed herein a blood pressure transducing bladder assembly which is specifically designed to easily access the supraorbital artery of substantially all patients using the eyebrow and nose of each patient as a frame of reference.

14 Claims, 1 Drawing Sheet

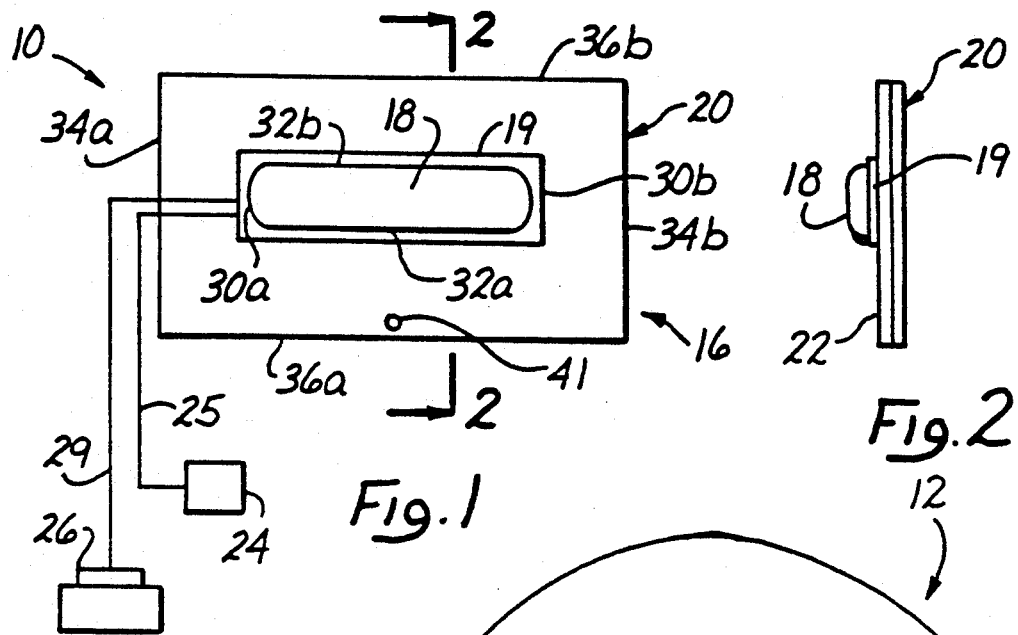
Fig. 1
Fig. 2
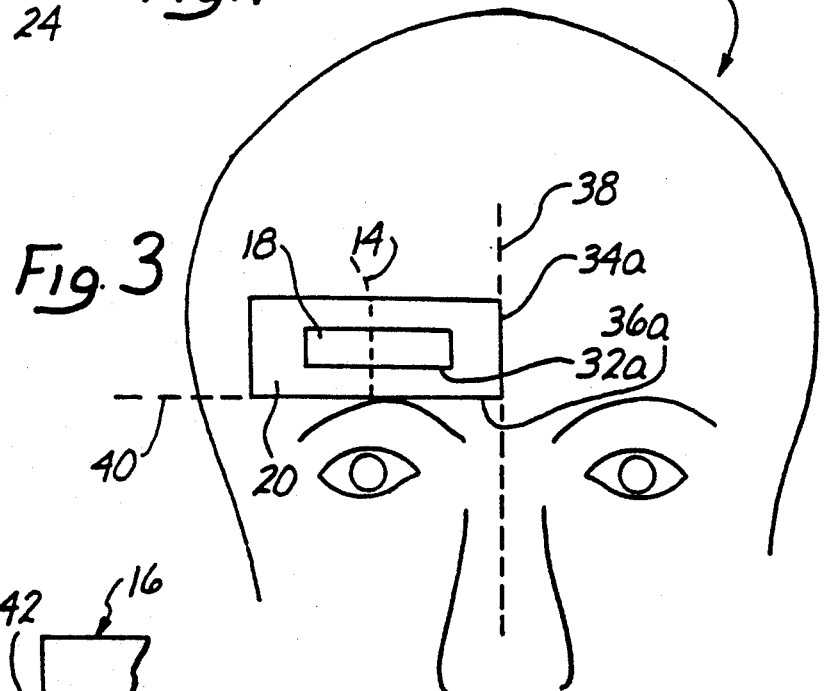
Fig. 3
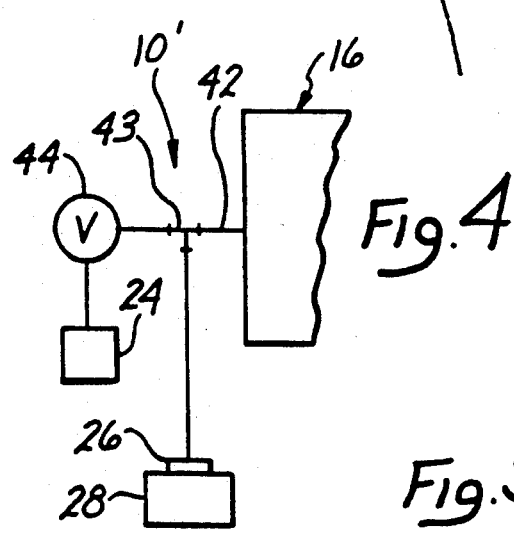
Fig. 4
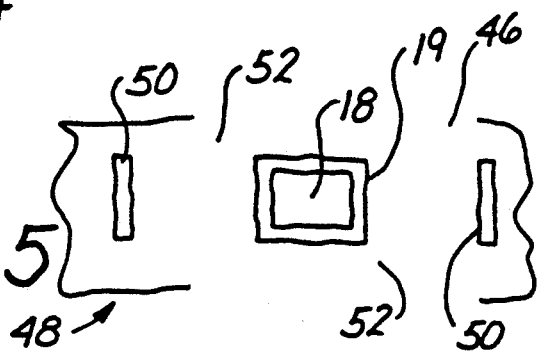
Fig. 5

BLOOD PRESSURE MONITORING TECHNIQUE WHICH UTILIZES A PATIENT'S SUPRAORBITAL ARTERY

The present invention relates generally to blood pressure monitoring techniques, and more particularly to an oscillometric blood pressure monitoring technique which is especially designed to take the blood pressure of a patient at his or her supraorbital artery and a blood pressure transducing bladder assembly designed specifically to carry out this latter technique.

Oscillometric techniques for obtaining various information about the blood pressure of a given patient are well known in the art, as exemplified in U.S. Pat. Nos. 3,903,872; 4,009,709; and 4,074,711, each of which is incorporated herein by reference. In all of these techniques, the blood pressure cuff, pad or like bladder type member are externally positioned against an artery of the subject being monitored and pressurized in a controlled manner so as to produce a series of pressure pulses which are responsive to an actual blood pressure within the cooperating artery. These pressure pulses can then be analyzed to obtain the desired information including, for example, diastolic and systolic pressures.

In U.S. Pat. No. 3,903,872 a technique is described for determining the diastolic pressure of a subject by appropriately analyzing these pressure pulses. In U.S. Pat. Nos. 4,009,209 and 4,074,711, techniques are described for determining systolic pressure. In all three of these patents, a conventional blood pressure cuff is utilized as a pressurizable pressure transducing bladder disposed around the arm or thigh of the subject.

The oscillometric measurement of blood pressure requires proper calibration between the pressure applied to the external surface of the body and the resultant pressure applied to the underlying target artery. The normal arrangement utilizes a pressure cuff wrapped entirely around the limb which contains the artery, as suggested in the patents recited above. This is because the pressure cuff can be made sufficiently long such that the applied pressure in the cuff results in a nearly equal pressure being applied to the artery, at least near the center of the cuff. One advantage in using a blood pressure cuff around the limb of a subject being monitored is that the cuff is old technology and is relatively uncomplicated in design. One disadvantage to its use is that the limb tends to be susceptible to muscular artifacts. Another disadvantage resides in the relatively large fluid supply needed to pressurize the cuff. Typically, a pressurized adult arm cuff requires a fluid volume of about 500 cubic centimeters. To pressurize a volume of that magnitude to a pressure above the anticipated systolic pressure of a person, often a pressure of about 160, requires a relatively large pressure pump. Still another disadvantage to using a pressure cuff around a limb arises when it is desirable or necessary to have reliable information regarding the blood pressure at the brain. The limbs are so far from the head that the information provided may not always be truly representative of the blood pressure at the brain. As a result of this particular disadvantage, the temporal artery has been suggested as a target artery for taking the blood pressure of a patient. See, for example, Iberall U.S. Pat. Nos. 3,658,054 and 3,704,708. Also, see published European Specification Number (publication no.) 0247880 published December, 1987 which is assigned to the assignee of the present application. This latter European specification is directed to a very specifically designed blood pressure transducing bladder assembly especially suitable for taking the pressure of a patient, non-invasively, at the patient's temporal artery.

There are two distinct advantages in using the temporal artery in taking the blood pressure of a patient. First, this approach provides for more reliable information regarding the blood pressure at the patient's brain than is possible using the patient's limb. Second, the temporal artery is one of the largest arteries in the head and therefore produces strong oscillometric pulses. One disadvantage, however, with selecting the temporal artery as the target artery resides in its particular location. As a general rule, the temporal artery includes an accessible target segment which is located just in front of the patient's ear and which extends upward and forward from there. However, the specific path taken by the temporal artery may differ substantially from side to side for a given patient and from patient to patient. As a result of this, it is often difficult to select the best location to access the temporal artery for any given patient. Moreover, given that the hairlines of most individuals vary, the hair and eyebrows can be obstructions to the process.

In view of the foregoing, it is an object of the present invention to provide a method of obtaining blood pressure information of a given patient by means of particular blood pressure technique, specifically by means of oscillometry, in a way which avoids the disadvantages recited immediately above.

A specific object of the present invention is to provide a technique for taking the blood pressure at the head of the patient without the disadvantages associated with using the temporal artery.

A further object of the present invention is to provide a blood pressure measuring device which is disposable, thus alleviating sanitation concerns, and being disposable, it is inexpensively manufactured and simply constructed.

Still a further object of the present invention is the provision of a more comfortable method of measuring blood pressure which avoids venous congestion and nerve trauma.

As will be seen in more detail hereinafter, there is disclosed herein a method of obtaining certain information about the blood pressure of a given patient by means of a particular blood pressure technique, specifically, by means of oscillometry, in which a pressurizable pressure transducing bladder located adjacent and cooperating with a particular target artery of the patient is used in combination with means for pressurizing the bladder in a controlled way in order to provide the desired information. In accordance with one aspect of the present invention, the particular target artery selected is the patient's supraorbital artery. Applicants have discovered that there is a segment of this artery that does not vary in location to any significant degree from side to side for a given patient or from patient to patient. Moreover, the particular target segment of this artery is virtually never obstructed by the patient's hairline. In substantially all cases, it can be easily located and accessed using certain facial features of any given patient, specifically, the patient's eyebrow and nose, as will be described in detail hereinafter.

The second aspect of the present invention, also to be described in detail hereinafter, resides in the utilization of a particular blood pressure transducing bladder assembly which has been specifically designed to easily locate and, when inflated, to sense pressure changes within the target segment of any given patient's supraorbital artery. As will be seen, this assembly includes a pressure transducing bladder and an adhesive pad which uses the upper most edge of the patient's eyebrow and the centerline of the patient's nose to ensure that the pressure transducing bladder properly extends across the target segment of the patient's supraorbital artery.

The present invention will be described in more detail hereinafter in conjunction with the drawings, wherein:

FIG. 1 diagrammatically illustrates a system for obtaining certain information about the blood pressure of a given patient by means of oscillometry, which system is shown including a blood pressure transducing bladder assembly, designed in accordance with the present invention, to locate and use the patient's supraorbital artery as the target artery in the blood pressure procedure;

FIG. 2 is a sectional view of the blood pressure transducing bladder assembly of FIG. 1, taken generally along line 2—2 in FIG. 1;

FIG. 3 diagrammatically illustrates a portion of the face of a given patient, specifically depicting the positional relationship between the patient's eyebrow and nose and the blood pressure transducing bladder assembly illustrated in FIGS. 1 and 2; and FIG. 4 illustrates a modified, preferred embodiment of the bladder assembly shown in FIG. 2;

FIG. 5 illustrates a further embodiment of the bladder assembly which uses a headband in place of a full pad.

Turning now to the drawing, wherein like components are designated by like reference numerals throughout the figures, attention is immediately directed to FIG. 1. This figure above, depicts a system for obtaining certain information about the blood pressure of a given patient. The system is generally indicated by the reference numeral 10 in FIG. 1 and the face of the patient is shown at 12 in FIG. 3. As discussed briefly above, and as will be described in more detail hereinafter, overall system 10 is specifically designed to use the supraorbital artery of patient 12 as the target for artery obtaining the desired blood pressure information. One of the two supraorbital arteries of patient 12 is shown by dotted lines at 14 in FIG. 3. While this artery is shown as a single artery, it is to be understood that the supraorbital artery incudes branches just above the eyebrow which along with the main artery define a supraorbital artery bed. As used herein (in both the specification and the claims) the term supraorbital artery is intended to refer to overall arterial bed, that is, the main artery and its branches.

Still referring to FIG. 1, system 10 includes a blood pressure transducing bladder assembly 16 which is shown including a pressurizable pressure transducing bladder 18 fixedly mounted to a slightly larger, similarly shaped and slightly more rigid bladder backing 19 and a pad 20 (exaggerated in thickness in FIG. 2) having an adhesive backing 22 against which the bladder 18 and bladder backing 19 are fixedly mounted within the outermost configuration of the pad. The backing 19 insures that the bladder extends out from the pad and backing against the artery when it is pressurized. Also, in a preferred embodiment, it is initially molded or otherwise provided in a convex shape so as to act as a spring in urging the bladder against the patient's supraorbital artery.

As will be seen hereinafter, blood pressure transducing bladder assembly 16 is designed in accordance with the present invention so as to readily locate and access supraorbital artery 14 of patient 12, that is, so as to ensure that pressure transducing bladder 18 extends against and across the supraorbital artery in a manner sufficient to monitor the blood pressure within that artery.

In addition to blood pressure transducing bladder assembly 16, overall system 10 includes suitable means 24 for pressurizing bladder 18 through tube 25 in a controlled way for producing a series of pressure pulses that are responsive to the actual blood pressure within the cooperating supraorbital artery 14. Typically air is used as the pressurizing medium to produce the pressure pulses, although liquid could be used, for example water, to increase the sensitivity of the procedure. These cuff pulses are converted to corresponding electronic signals by a suitable transducer 26 coupled to the bladder by means of the tube 29 and then these signals are acted upon by suitable circuitry 28 in order to extract therefrom the desired information about the blood pressure of individual 12. The particular way in which bladder 18 is pressurized to produce the desired pressure pulses is known in the art and will not be described herein. It suffices to say that the pressure within the bladder is ramped upward or downward between a minimum pressure of zero torr and a maximum which is slightly above the anticipated systolic pressure of the subject being evaluated, for example around 160 torr. Also, both transducer 26 and circuitry 28 are known in the art and hence will not be discussed herein. Examples of suitable circuitry may be found in the previously recited patents. In this regard, it should be noted that the supraorbital artery is normally not as large an artery as its neighbor, the temporal artery. Nevertheless, the transducer 26 and circuitry 28 known in the art have been found to be quite compatible with the somewhat less powerful supraorbital artery. Referring now to FIG. 3 in conjunction with FIGS. 1 and 2, attention is specifically directed to pressure transducing bladder assembly 16 and, in particular, the way in which this assembly is designed to easily and automatically locate and access supraorbital artery 14. As illustrated in both FIGS. 1 and 3, the pressure transducing bladder 18 is generally rectangular in outer configuration so as to define opposing widthwise edges 30A, 30B and opposing lengthwise edges 32A, 32B. At the same time, adhesive backed pad 20 also has a generally rectangular outer configuration so as to define opposing widthwise edges 34A, 34B and opposing lengthwise edges 36A, 36B. Note specifically in the embodiment illustrated that the bladder 18 is substantially smaller than the pad 20 and is centrally located within the outer configuration of the pad such that all four of the widthwise edges are parallel to one another and all four of the lengthwise edges are parallel to one another. In particular, with the bladder fixedly maintained on the pad, there exists a fixed positional relationship between the bladder itself and the opposing widthwise edges 34A, 34B and the bottom lengthwise edge 36A of the pad. As will be seen immediately below, this fixed positional relationship is important to the present invention. The blood pressure transducing bladder assembly 20 is shown in FIG. 3 in its operating position on the face of patient 12. For purposes of clarity, pressurizing means 24, transducer 26, circuitry 28 and their associated tubes 25 and 29 have been omitted from this figure. With particular regard to the positional relationship between assembly 16 and the facial features of patient 12, it should be noted that the widthwise edge 34A of pad 20 is lined up vertically with the center line 38 of a patient's nose, while at the same time, lengthwise edge 36A is lined up horizontally with eyebrow line 40 which passes over the uppermost edge of one of the patient's eyebrows. This, in turn, places the bladder 18 in a fixed positional relationship with the nose center line 38 and the eyebrow line 40. In this regard, applicants have discovered through an extensive analysis of numerous patients that there is a generally fixed positional relationship for any given patient between center line 38 and eyebrow line 40 on the one hand and the target segment of the patient's supraorbital artery on the other hand. Specifically, the target segment of that artery extends generally upward from the eyebrow to one side of line 38 and above line 40. This generally vertical path taken by the artery moves laterally, that is, horizontally, from patient to patient, at most a small amount, that is, no more than at most about one-half inch.

By lining up edges 34A and 36A of pad 20 with facial lines 38 and 40, respectively, bladder 18 is automatically positioned directly against the patient's skin immediately above and across the supraorbital artery 14 in the desired manner. In order to take into account the slight lateral variations of the artery from patient to patient, bladder 18 is designed to be sufficiently long between widthwise edges 30A and 30B. Note also that the segment of the supraorbital artery immediately under bladder 18 is entirely beyond the hairline or eyebrow in substantially all patients.

The present invention resides in the use of the supraorbital artery as the target artery, the way in which blood pressure transducing bladder assembly 16 is dimensionally configured to ensure that bladder 18 intersects the supraorbital artery when pad 20 is lined up with facial lines 38 and 49 in the manner described above, and in the ability of the bladder to expand to meet the target area and deliver a calibrated and uniform pressure to the target artery. It has been found that the best results are obtained when the total inflated volume of the bladder is less than six milliliters. The present invention does not reside in the way in which the assembly functions as part of the overall system for obtaining blood pressure information generally, as this function is well known in the art. Pressure transducing bladder 18 may be constructed of any suitable material, preferably non-distensible, flexible elastomeric material, for example, polyvinyl chloride or polyurethane and is readily connectible with tubes 25 and 29 in any known manner. Moreover, it is bonded or otherwise suitably fixedly mounted to backing 19 which is similarly fixed to adhesive pad 20. The adhesive pad used to constrain the sensor bladder over the artery is flexible to conform to the skull curvatures in the vicinity of the sensor location, and yet should preferably be made of a nonstretching material in order to provide an accurate reading.

In an actual working embodiment, bladder 18 is 0.4 inch wide (its widthwise edges) and is 1.0 inch long (its lengthwise edges). When fully pressurized but unconstrained, it is preferably about 0.3 inch deep but, in general, between 0.1 and 0.6 inches deep. Moreover, in this condition, the bladder defines a volume between about 0.5 and 8 milliliters. In any event, it must be sufficiently deep to adequately engage the contour of the supraorbital region of the skull in order to function properly. The pad in this same embodiment is 1.2 inches wide (its widthwise edges) and 1.8 inches long (its lengthwise edges). Bladder 18 in this actual working embodiment is located 1 cm nominally from the lower pad edge in the manner illustrated in FIGS. 1 and 3. It has been found that this particular dimensional relationship between the bladder and pad ensures that the bladder crosses the supraorbital artery of substantially all patients when the pad is positioned on the patient in the manner described above. While this dimensional relationship between bladder and pad may be preferred, it is to be understood that this relationship can be changed without departing from the present invention so long as the dimensional relationship selected achieves the object of the invention which is to ensure that the supraorbital artery is found and accessed by the bladder. For example, it may be desirable to increase the distance between the upper lengthwise edges of the bladder and pad so that the bladder is obviously closer to the lower lengthwise edge of the pad. This insures the proper alignment of the pad with the eyebrow. Also, the pad must be large enough to provide sufficient adhesive to prevent the bladder from lifting off the patient's skin when pressurized. Alternatively or in conjunction with the pad, a headband could be used to fix the bladder in place. Moreover, while both the bladder 18 and the pad 20 are shown as strong rectangles having squared corners, both could be more oval shaped or some other shape so long as the pad itself can be readily lined up with nose line 38 and eyebrow line 40 or other suitable facial features in a way which ensures that bladder 18 crosses supraorbital artery 14. For example, the eyebrow could be used alone by lining up a mark provided on the pad with the top center point on the eyebrow. Such a mark is shown at 41 in FIG. 1. As another example, the lower edge 36a of the pad could be contoured to the shape of the eyebrow.

Referring specifically to FIG. 4, a modified system for obtaining certain information about the blood pressure of a given patient is generally indicated by the reference numeral 10'. This system may be identical to system 10 in most respects. For example, it may include the same blood pressure transducing bladder assembly 16 as well as the same pressurizing means 24, transducer 26 and circuitry 28. However, system 10' uses only one, rather than two, tubes extending out of the bladder assembly. That tube is generally indicated at 42. Tube 42 is connected to one side of a key connection 43 into other sides, one connected to pressurizing means 24 through a suitable solenoid or other such valve 44 than the otherwise free side connected to transducer 26. The way in which this arrangement functions is as follows. When the bladder 18 (see FIG. 1) is pressurized by means 24, the valve 44 is maintained at its open or flow through condition. Once the bladder is pressurized to its maximum level, typically slightly above the patient's anticipated systolic pressure, the valve 44 is closed, allowing the pressurized air within the bladder to communicate directly with transducer 26 in the form of oscillometric pulses, as is well known in the art. In an actual working embodiment, tube 42 communicates with the interior of bladder 18 through the backside of backing 19. In this regard, pad 20 is formed of two adhesive layers as shown in FIG. 2 with a portion of the tube sandwiched therebetween. In fact, this dual padded configuration can also be used where two tubes are provided, as in the case of system 10 shown in FIG. 1.

Turning now to FIG. 5, a modified bladder assembly 48 is illustrated. This particular bladder assembly includes the same bladder 18 and bladder backing 19 mounted on a headband 46 rather than on the previously described pad 20. Adhesive strips 50 may be used as alignment edges corresponding to pad edges 34. The upper and lower edges 52 of the headband are configured to serve as alignment edges corresponding to pad edges 36. Assembly 48 could include a full pad 20 rather than strips 50.

It is to be understood that the above described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. In a method of obtaining certain information about the blood pressure of a given person by means of oscillometry in which a pressurizable pressure transducing bladder located adjacent and cooperating with a particular target artery of the person is used in combination with means for pressurizing the bladder in a controlled way for producing a series of pressure pulses that are responsive to the actual blood pressure within the cooperating target artery and that, upon analysis thereof, provide the desired information, the improvement comprising the steps of:

(a) selecting as said particular artery, a supraorbital artery of the person;

(b) providing a relatively small adhesive attached pressure transducing bladder which when placed externally against the supraorbital artery in a particular manner and pressurized in said controlled way produces said series of pressure pulses; and (c) placing said bladder externally against said supraorbital artery in said particular manner and pressurizing it in said controlled way for producing said pressure pulses, said pressure transducing bladder being placed externally against said supraorbital artery in a predetermined position with respect to certain predetermined facial features of said given person in order to insure that the bladder is properly placed externally against the supraorbital artery, said pressure transducing bladder forming part of an overall blood pressure transducing bladder assembly which also includes means in a fixed positional relationship with said bladder for securing said transducing bladder in said predetermined position and means adhesively engaging the skin of said person immediately adjacent said predetermined facial features for aligning said securing means with said predetermined facial features for insuring that said bladder is placed in said predetermined position, said securing means including an adhesive backed pad which is large relative to said bladder said predetermined facial features of said given person including the person's eyebrow and nose, and wherein said aligning means includes a segment of said adhesive backed pad.

2. The improvement according to claim 1 wherein said adhesive pad is rectangular in outer configuration so as to define widthwise and lengthwise edges, wherein said step of placing said bladder externally against said supraorbital artery includes the step of securing said adhesive pad against the face of said given person such that one lengthwise edge of the pad extends horizontally immediately adjacent the uppermost edge of one of the person's eyebrows and such that one widthwise edge of the pad extends vertically in line with and above the centerline of the person's nose, whereby to place said transducing bladder in said predetermined position.

3. The improvement according to claim 2 wherein said transducing bladder is generally rectangular in outer configuration so as to define widthwise and lengthwise edges and smaller in both rectangular dimensions than said adhesive pad, said transducing bladder being fixedly secured to one side of said pad within the outer periphery of the pad such that the widthwise edges of said bladder are parallel with and predetermined distances from said one widthwise edge of said pad and such that the lengthwise edges of said bladder are parallel with and predetermined distances from said one lengthwise edge of said pad.

4. The improvement according to claim 3 wherein said widthwise edges of said bladder are about 0.4 inch and 1.2 inches from said one widthwise edge of said pad, respectively, and wherein said lengthwise edges of said bladder are about 0.4 and 0.8 inches from said one lengthwise edge of said pad, respectively.

5. The method according to claim 1 wherein said bladder assembly includes a relatively rigid bladder backing against which said bladder is mounted, said bladder backing being convex in shape so as to function as a spring urging the bladder against the person.

6. The improvement according to claim 1 including one and only one tube extending out of said overall blood pressure transducing bladder assembly for connection with said pressurizing means for pressurizing the bladder and for producing said series of pressure pulses.

7. In a system for obtaining certain information about the blood pressure of a given person by means of oscillometry in which a pressurizable adhesive attached pressure transducing bladder located adjacent and cooperating with a particular target artery of a person is used in combination with means for pressurizing the bladder in a controlled way for producing a series of pressure pulses that are responsive to the actual blood pressure within the cooperating target artery and that, upon analysis thereof, provide the desired information, the improvement comprising a blood pressure transducing bladder assembly including:

(a) said transducing bladder, which is relatively small; and (b) a pad having an adhesive backing against which said bladder is fixedly mounted within the outermost configuration of the pad, which is large relative to said bladder, said adhesive backing serving to secure said bladder to the face of said given persons;

(c) said bladder and said pad being configured such that by lining up predetermined segments of said pad with the uppermost edge of one of the given person's eyebrows and the centerline of the person's nose immediately above the latter, said bladder will automatically extend across the supraorbital artery of the person, said adhesive pad being rectangular in configuration so as to define widthwise and lengthwise edges, said bladder being also rectangular in configuration so as to define widthwise and lengthwise edges parallel to the widthwise and lengthwise edges of the pad, one of the lengthwise edges of said pad and one of its widthwise edges serving as said predetermined segments of said pad, the widthwise edges of said bladder being predetermined distances from said one widthwise edge of said pad and the lengthwise edges of said bladder being predetermined distances from said one lengthwise edge of said pad.

8. A blood pressure transducing bladder assembly for use in an oscillometric system for obtaining certain information about the blood pressure of a given person, comprising:

(a) a relatively small, pressurizable adhesive attached pressure transducing bladder having a generally rectangular outer configuration so as to define widthwise and lengthwise edges;

(b) a pad, which is large relative to said bladder, having a generally rectangular outer configuration so as to define widthwise and lengthwise edges and also having an adhesive backing against which the bladder is fixed mounted within the outermost configuration of the pad such that the widthwise and lengthwise edges of the pad and bladder are respectively parallel to one another, said adhesive backing serving to secure said bladder to the face of said given person; and (c) said bladder and said pad being configured such that by lining up a bottom lengthwise edge and an inner widthwise edge of said pad with the uppermost edge of an eyebrow of the person and the centerline of the person's nose, respectively, said bladder will automatically extend across the supraorbital artery of the person, the widthwise edges of said bladder being predetermined distances from said inner widthwise edge of said pad, and the lengthwise edges of said bladder being predetermined distances from said bottom lengthwise edge of said pad.

9. A bladder assembly according to claim 8 wherein the widthwise edges of said bladder are 0.4 inch and 1.2 inches, respectively, from said inner widthwise edge of said pad, and wherein the lengthwise edges of said bladder are 0.4 and 0.8 inches, respectively, from said bottom lengthwise edge of said pad.

10. The improvement according to claim 8 wherein said blood pressure transducing bladder assembly includes a bladder backing disposed between said bladder and said pad to which the bladder is fixedly mounted, said bladder pad being more rigid than said bladder and convex in shape so as to function as a spring to urge the bladder against said given person.

11. The improvement according to claim 8 wherein said blood pressure transducing bladder assembly includes one and only one tube extending out of said bladder for connection with said pressurizing means for producing said series of pressure pulses.

12. The improvement according to claim 8 wherein said bladder, when fully pressurized but unconstrained, is between about 0.1 and 0.6 inches deep and defines a fully pressurized but unconstrained volume between about 0.5 and 8 milliliters.

13. In a method of obtaining certain information about the blood pressure of a given person by means of oscillometry in which a pressurizable pressure transducing bladder located adjacent and cooperating with a particular target artery of the person is used in combination with means for pressurizing the bladder in a controlled way for producing a series of pressure pulses that are responsive to the actual blood pressure within the cooperating target artery and that, upon analysis thereof, provide the desired information, the improvement comprising the steps of:

(a) selecting as said particular artery, a supraorbital artery of the person;

(b) providing a relatively small adhesive attached pressure transducing bladder which when placed externally against the supraorbital artery in a particular manner and pressurized in said controlled way produces said series of pressure pulses; and (c) placing said bladder externally against said supraorbital artery in said particular manner and pressurizing it in said controlled way for producing said pressure pulses, said pressure transducing bladder being placed externally against said supraorbital artery in a predetermined position with respect to certain predetermined facial features of said given person in order to insure that the bladder is properly placed externally against the supraorbital artery, said pressure transducing bladder forming part of an overall blood pressure transducing bladder assembly which also includes means in a fixed positional relationship with said bladder for securing said transducing bladder in said predetermined position and adhesively engaging the skin of the person immediately adjacent said predetermined facial features means for aligning said securing means with said predetermined facial features for insuring that said bladder is placed in said predetermined position, said securing means including an adhesive backed pad, which is large relative to said bladder wherein said predetermined facial features of said given person including the upper edge of a person's eyebrow, and wherein said aligning means includes a segment of said adhesive backed pad which is located adjacent said uppermost eyebrow edge.

14. In a system for obtaining certain information about the blood pressure of a given person by means of oscillometry in which a pressurizable adhesive attached pressure transducing bladder located adjacent and cooperating with a particular target artery of a person is used in combination with means for pressurizing the bladder in a controlled way for producing a series of pressure pulses that are responsive to the actual blood pressure within the cooperating target artery and that, upon analysis thereof, provide the desired information, the improvement comprising a blood pressure transducing bladder assembly including:

(a) said transducing bladder, which is relatively small; and (b) a pad, which is large relative to said bladder, having an adhesive backing against which said bladder is fixedly mounted within the outermost configuration of the pad, said adhesive backing serving to secure said bladder to the face of said given person;

(c) said bladder and said pad being configured such that by lining up a predetermined segment of said pad with the uppermost edge of one of the given person's eyebrows, said bladder will automatically extend across the supraorbital artery of the person.

* * * * *